United States Patent

Seufer-Wasserthal et al.

[11] Patent Number: 5,534,436
[45] Date of Patent: Jul. 9, 1996

[54] ENZYMATIC RESOLUTION OF ASYMMETRIC ALCOHOLS BY MEANS OF VINYL ESTERS OF POLYBASIC CARBOXYLIC ACIDS

[75] Inventors: Peter Seufer-Wasserthal, Schwanenstadt; Herbert Mayrhofer, Engerwitzdorf; Irma Wirth, Enss; Peter Pöchlauer, Linz, all of Austria

[73] Assignee: Chemie Linz GmbH, Linz, Austria

[21] Appl. No.: 413,439

[22] Filed: Mar. 30, 1995

[30] Foreign Application Priority Data

Mar. 30, 1994 [AT] Austria .................................. A672/94

[51] Int. Cl.$^6$ ...................................................... C12P 41/00
[52] U.S. Cl. ............................................................. 435/280
[58] Field of Search .............................................. 435/280

[56] References Cited

U.S. PATENT DOCUMENTS

| | | | |
|---|---|---|---|
| 4,996,158 | 2/1991 | Oda et al | 435/280 |
| 5,032,523 | 7/1991 | Amano et al. | 435/280 |

FOREIGN PATENT DOCUMENTS

| | | |
|---|---|---|
| 0231089A2 | 8/1987 | European Pat. Off. . |
| 0266217B1 | 5/1988 | European Pat. Off. . |
| 0288994A2 | 11/1988 | European Pat. Off. . |
| 0304706A2 | 3/1989 | European Pat. Off. . |
| 0321918A2 | 6/1989 | European Pat. Off. . |
| 0328125A2 | 8/1989 | European Pat. Off. . |
| 0357009A3 | 3/1990 | European Pat. Off. . |
| 0357009A2 | 3/1990 | European Pat. Off. . |
| 0407033A2 | 1/1991 | European Pat. Off. . |
| 0454463A2 | 10/1991 | European Pat. Off. . |
| 0560408A1 | 9/1993 | European Pat. Off. . |
| 0577446A2 | 1/1994 | European Pat. Off. . |
| 1806201A3 | 1/1989 | U.S.S.R. . |

OTHER PUBLICATIONS

Abstract of JP 5-161499 (Jun. 1993).
Abstract of JP 5-86002 (Apr. 1993).
Abstract of JP 4-262794 (Sep. 1992).
Patent Abstracts of Japan, vol. 17, No. 409, C-1091, abstract of JP 5-84094 (Apr. 1993).
Patent Abstracts of Japan, vol. 17, No. 205, C-1051, abstract of JP 4-349894 (Dec. 1992).
Patent Abstracts of Japan, vol. 16, No. 63, C-911, abstract of JP 3-259094 (Nov. 1991).
Patent Abstracts of Japan, vol. 14, No. 531, C-780, abstract of JP 2-222698 (Sep. 1990).
Patent Abstracts of Japan, vol. 14, No. 106, C-694, abstract of JP 1-309694 (Dec. 1989).
Patent Abstracts of Japan, vol. 13, No. 569, C-666, abstract of JP 1-235599 (Sep. 1989).

*Primary Examiner*—Michael G. Wityshyn
*Assistant Examiner*—S. Saucier
*Attorney, Agent, or Firm*—Wenderoth, Lind & Ponack

[57] ABSTRACT

Resolution of asymmetric alcohols by reacting them with a vinyl, propenyl or isopropenyl ester of an alkone- or alkene- di- or tricarboxylic acid in the presence of a lipase, and the use thereof.

5 Claims, No Drawings

ENZYMATIC RESOLUTION OF ASYMMETRIC ALCOHOLS BY MEANS OF VINYL ESTERS OF POLYBASIC CARBOXYLIC ACIDS

Asymmetric alcohols are important intermediate compounds for a number of pharmaceutically active compounds, for example for substances which affect the central nervous system (CNS). The knowledge that usually only one enantiomeric form of these substances in each case exerts the desired pharmaceutical action has led to increased demand for preparation processes for their active enantiomer avoiding the formation of their inactive, often even toxic, other enantiomer. Processes for the preparation of enantiomerically enriched asymmetric alcohols thus have particular importance as preliminary stages for these compounds.

Processes for the enzymatic resolution of alcohols are already known. Thus according to Synthesis 1989, 933–934, a racemic alcohol is converted to the corresponding butyric acid ester and the racemic ester is then hydrolyzed enantioselectively in the presence of a lipase. One enantiomer of the alcohol is obtained in free form, the other remains esterified and can be separated using conventional chemical processes, for example chromatography, and is optionally also obtainable in free form by subsequent chemical hydrolysis. In order to obtain the desired enantiomer, up to four process steps, namely chemical esterification, enzymatic hydrolysis, separation of ester and alcohol and chemical hydrolysis of the ester, are therefore necessary. In addition, enzymes are in general soluble in the aqueous phase of the hydrolysis reaction mixture and can only be recovered therefrom with difficulty for possible reuse. They must therefore be immobilized on a water insoluble support.

Alternatively, enzymes can be employed in a water-immiscible organic solvent in which they are usually insoluble. If it is wished to avoid the necessity of introducing or removing water in molar amounts during the reaction, it is possible, however, preferably only to catalyze those processes which take place without formation or consumption of water in molar amounts, i.e. acylations, for example with carboxylic anhydrides, or transesterifications. According to J. Org. Chem. 53 (1988) 5531, a racemic alcohol can be esterified enantioselectively by means of a carboxylic anhydride in an organic solvent under the effect of a lipase, by means of which the two enantiomers can be separated from one another. Often, however, the carboxylic acid formed at the same time has an interfering effect on the enzyme activity. In J. Am. Chem. Soc. 107 (1985) 7072, "activated esters" i.e. esters of not very nucleophilic alcohols, have been proposed as acylating agents for enzymatic resolutions of alcohols. However, esters of this type, for example 2-haloethyl esters, can hardly be employed industrially. In addition, these reactions are reversible and thus incomplete.

In EP-A-0 321,918, a process for the enzymatic resolution of alcohols by acylation with or in vinyl acetate or vinyl chloroacetate under the effect of a lipase is described. The vinyl alcohol formed in the course of the reaction tautomerizes to acetaldehyde, which escapes from the reaction mixture as a gas and makes the reaction irreversible. After the enzymatic acylation, one enantiomer of the alcohol is again present as an ester, in this case as the acetate or chloroacetate, and the other in free form. However, it has been shown that the separation of the resulting free alcohol from its enantiomeric acetate or chloroacetate is especially difficult on a relatively large scale, as the alcohol/ester pair to be separated often differ little in their physical properties such as boiling points or solubilities or form azeotropes which are difficult to separate at all. This poor separability is to be taken into account according to the as yet unpublished European Patent Application No. 94101158.7 in as much as the use of longer-chain vinyl esters, for example of vinyl laurate or vinyl palmirate, is recommended for the enantiomeric preparation of alkinols. As a result the alcohol can usually be separated from the ester by distillation, and the process can be used industrially. The high molecular weight of vinyl esters of this type has the effect, however, that, particularly in the preparation of alcohols of low molecular weight, they have to be employed in a considerable excess by weight, so that in the corresponding reaction mixtures, especially toward the end of the reaction, the now enantiomerically enriched alcohol is only present in very small amounts, which on the one hand makes its isolation difficult, and on the other hand leads to a poor spacetime yield for corresponding processes.

Unexpectedly, it has now been found that these disadvantages can be avoided if, for the enzymatic resolution of asymmetric alcohols, not the vinyl esters of monocarboxylic acids, but the vinyl esters of di- and polybasic carboxylic acids are employed. As all vinyl ester units of the molecule participate in the enzymatic replacement, esters are obtained which can easily be separated from the unreacted alcohol, as they have large molecular weight differences from the alcohol. Moreover, owing to the presence of several vinyl ester groups in one molecule of the acylating agent, the density of the vinyl ester groups is very large, so that the alcohol to be cleaved is present in the reaction mixture in a high concentration.

The invention therefore relates to a process for the resolution of asymmetric alcohols of the formula

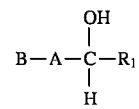   I wherein $R_1$ is COOH, COOC$_1$–C$_4$-alkyl, CN, C$_1$–C$_4$-alkyl which can be straight-chain or branched, saturated or unsaturated and optionally mono- or polysubstituted by halogen, C$_1$–C$_4$-alkoxy, methylenedioxy, ethylenedioxy, NH$_2$, C$_1$–C$_4$-alkylamino, NH—SO$_2$CH$_3$, COCH$_3$, COCH$_3$, COOH, COOC$_1$–C$_4$-alkyl, NO$_2$, CN, N$_3$, A is either a single bond, C$_1$–C$_4$-alkylene or C$_2$–C$_6$-alkenylene, and B is phenyl, naphthyl, pyridyl, pyrimidyl, furyl, thienyl, imidazolyl, C$_1$–C$_{20}$-alkyl which can be straight-chain or branched, and saturated or unsaturated by one or more double or triple bonds, where one or more methylene groups can be replaced by a keto group, by O, by NH or by N-alkyl (C$_1$–C$_4$), C$_3$–C$_7$-cycloalkyl which can be saturated or unsaturated, where a methylene group can optionally be replaced by a keto group and one or two methylene groups can optionally be replaced by O or NH, where the radical B can be mono- or polysubstituted by halogen, C$_1$–C$_4$-alkoxy, methylenedioxy, ethylenedioxy, NH$_2$, C$_1$–C$_4$-alkylamino, NH—SO$_2$CH$_3$, CO–CH$_3$, COOH, COOC$_1$–C$_4$-alkyl, NO$_2$, CN, N$_3$, or A is a single bond and $R_1$ and B together are a C$_3$–C$_8$-alkylene or -alkenylene group, in which 2 methylene groups can additionally be bridged by means of a further $C_1$–$C_4$-alkylene chain, where one or more methylene groups can be replaced by a keto group, or by O, NH or N-alkyl ($C_1$–$C_4$) and where the ring formed from $R_1$ and B can optionally be mono- or polysubstituted by halogen, $C_1$–$C_4$-alkyl which can be straight-chain or branched, by $C_1$–$C_4$-alkoxy, methylenedioxy, ethylenedioxy, $NH_2$, $C_1$–$C_4$-alkylamino, NH—$SO_2CH_3$, CO—$CH_3$, COOH, COOC$_1$–$C_4$-alkyl, $NO_2$, CN, $N_3$, which comprises reacting an asymmetric alcohol of the formula I with a vinyl, propenyl or isopropenyl ester of a $C_2$–$C_{10}$-alkane- or -alkene-di- or -tricarboxylic acid in the presence of a lipase and isolating the remaining alcohol of the formula I which is now enantiomerically pure and if desired recovering the other enantiomer from the ester formed.

Asymmetric alcohols of the formula I are known and/or can be prepared by known methods. They can be employed as a racemic mixture or as a mixture in which one of the two enantiomers is already present in enriched form. These are, for example, beta-blockers or components therefor, such as phenyl, or naphthylalkanolamines in which B is a substituted phenyl or naphthyl ring, A is a single bond and $R_1$ is an alkylaminomethyl radical, or intermediates for these an which $R_1$ is a haloalkyl radical. Beta-blockers of this type are, for example, sotalol or nifenalol. Other asymmetric alcohols which can be prepared are alkylalkynylcarbinols ($R_1$=alkyl, B=alkynyl and A=a single bond), which are, for example, components for lipoxygenase inhibitors, or compounds of the type 2-hydroxycarbonitrile ($R_1$=CN, B=substituted alkyl), which are important intermediates for the preparation of amino acids, such as gamma-amino beta-hydroxybutyric acid (GABOB). Similar compounds in which $R_1$=CN, A=$(CH_2)_2$ and B=phenyl are intermediates for the synthesis of ACE inhibitors such as enalapril. Many cyclic and bicyclic alcohols such as 2-alkyl-4-hydroxy-cyclohexenones are intermediates for the preparation of prostaglandins.

Vinyl, propenyl or isopropenyl esters of alkane-or alkenedi- or -tricarboxylic acids are, for example, the esters of oxalic acid, malonic acid, succinic acid, glutaric acid, adipic acid, pimelic acid, suberic acid, azelaic acid, sebacic acid, fumaric or maleic acid or aconitic acid. The esters of adipic acid, succinic acid and aconitic acid are preferred. Preferred esters are the vinyl esters.

Lipases are to be understood as meaning lipases suitable for resolution, lipases from pig's liver, pig's pancreas and from microorganisms such as Candida, Mucor, Rhizopus, Penicillium, Aspergillus and Pseudomonas are preferred. Commercially available lipases are particularly preferred, very preferably lipases from Candida or Pseudomonas. The lipase can be employed here in purified or partly purified form or in the form of the microorganism itself, in free or immobilized form.

The process according to the invention can be carried out according to a procedure disclosed in EP-A-0 321 918. To do this, a lipase and an alcohol of the formula I are initially taken together with a vinyl ester of the formula II. Per mole of alcohol, at least the amount of vinyl ester is employed here which contains half a mole of vinyl ester groups. The amount of lipase needed is dependent on the chemical composition of the alcohol and of the vinyl ester, on the desired reaction time and on the nature of the lipase and can be easily determined for each case by a preliminary experiment.

The reaction mixture is advantageously stirred or shaken with the lipase at temperatures from −10° C. up to the deactivation temperature of the lipase employed, preferably at the temperature at which the lipase has its highest activity and which is in general specified by the manufacturer. However, it is also possible initially to introduce the lipase into a module, for example into a column, and to lead the mixture which contains the alcohol and the vinyl ester through this module in circulation. In this process, the vinyl ester groups of the acylating agent are sequentially converted to esters of one enantiomer of the asymmetric alcohol, while the other enantiomer of the asymmetric alcohol essentially remains unchanged. The vinyl alcohol released is tautomerized to the corresponding carbonyl compound, which no longer participates in the occurrence of the reaction.

The progress of the reaction, that is to say the sequential exchange of the vinyl ester groups for ester groups of one enantiomer of the asymmetric alcohol, is monitored by customary methods, for example by gas chromatography. As a lipase can actually preferably react one of the two enantiomers, but in general also the second enantiomer, at suitable intervals the enantiomer excess ee of the unreacted alcohol or of the ester formed is measured with the aid of suitable methods, for example by determination of the optical rotation or by chromatography on a chiral phase. After reaching the desired degree of reaction, which is dependent on the desired product and its desired enantiomer excess, the reaction is terminated. To work up the reaction mixture, the lipase is optionally separated from the reaction mixture, for example by filtering off or centrifuging off, and the residue is subjected to a separation operation such as, for example, extraction, distillation or chromatography. A distillation is preferred here, which is particularly effective particularly as a result of the use according to the invention of vinyl esters of polybasic carboxylic acids, as the boiling points of the alcohol, its ester, vinyl ester and the carbonyl compound formed from the vinyl ester differ sufficiently for a simple, distillative, highly effective separation. If any enantiomer is desired which was preferably esterified in the course of the reaction, after isolation of this ester from the reaction mixture an ester hydrolysis optionally also in the presence of a lipase, can be carried out.

It has been shown that the addition of an organic solvent to the reaction mixture positively affects the reaction rate. In a preferred embodiment, an organic solvent is therefore added to the reaction mixture, by means of which the viscosity of the reaction mixture is lowered in an advantageous manner. Suitable organic solvents are optionally halogenated aliphatic or aromatic hydrocarbons such as e.g. pentane, hexane, cyclopentane, toluene, xylenes, dichloromethane, dichloroethane, chlorobenzenes, ethers, such as e.g. diethyl ether, tetrahydrofuran, dioxane, esters, such as e.g. ethyl acetate, butyl acetate, or mixtures of such solvents, halogenated aliphatic or aromatic hydrocarbons being preferred. The organic solvent is added in amounts from 0.1 to 70% by volume, preferably from about 0.5 to 60% by volume relative to the total reaction mixture.

With the aid of the process according to the invention, a mixture of two enantiomers of an asymmetric alcohol can be converted by enzyme-catalyzed stereo-selective acylation in good space-time yield to a technically easily separable mixture which contains one enantiomer of the asymmetric alcohol in unchanged form and the other enantiomer in the form of an ester. The process yields enantiomerically pure alcohols or esters, an enantiomer excess of over 90% in the unchanged alcohol or in the ester being obtained depending on the degree of reaction. The process is therefore an enrichment of the art.

EXAMPLES

Examples 1–4

0.92 g (4.63 mmol) of divinyl adipate, 0.02 ml of sodium phosphate buffer (0.1 M, pH 7.0), 4.5 ml of o-xylene and 0.3 g of Pseudomonas lipase (Amano PS) were added to 7.13 mmol of a racemic alcohol. The reaction mixture was shaken at 40° C. The enantiomer excess of the unreacted alcohol was determined as trifluoroacetyl derivative by means of GC on a cyclodextrin column. The results obtained are listed in Table 1.

TABLE 1

| Example No. | Alcohol | Reaction time | % ee |
|---|---|---|---|
| 1. | 3-methyl-2-butanol | 168 hours | 94 |
| 2. | 1-octyn-3-ol | 168 hours | 95 |
| 3. | 2-octanol | 23 hours | 98 |
| 4. | 2-chloro-1-phenylethanol | 188 hours | 95 |

Example 5

87.17 g (0.44 mol, 0.62 equivalents based on the alcohol) of divinyl adipate, 1.50 ml of sodium phosphate buffer (0.1 M, pH 7.0), 450 ml of o-xylene and 30 g of Pseudomonas lipase (Amano PS ) were added to 50 g (0.713 mol) of R,S-but-3-yn-2-ol. The reaction mixture was stirred at 40° C. The enantiomer excess ee of the unesterified alcohol was determined by means of GC on a cyclodextrin column. After attaining 95% ee, the reaction was terminated by filtering off the enzyme and the filtrate was fractionally distilled to isolate S-but-3-yn-2-ol, 12 g of S-but-3-yn-2-ol of 95% ee being obtained.

Examble 6

1.84 g (0.009 mol, 0.65 equivalents based on the alcohol) of divinyl adipate, 30 µl of sodium phosphate buffer (0.1 M, pH 7.0), 9 ml of o-xylene and 0.6 g of Pseudomonas lipase (Amano PS) were added to 1.0 g (0. 014 mol) of R,S-but-3-yn-2-ol. The reaction mixture was stirred at 40° C. The reaction was monitored by means of gas chromatography on a cyclodextrin column, and in so doing it was found that both vinyl ester groups react. But-3-yn-2-ylvinyl adipate is formed first, which reacts further to give dibut-3-yn-2-yl adipate.

What we claim is:

1. A process for the resolution of asymmetric alcohols of the formula

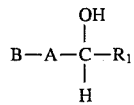

$$B-A-\underset{\underset{H}{|}}{\overset{\overset{OH}{|}}{C}}-R_1 \qquad I$$

wherein $R_1$ is COOH, COOC$_1$–C$_4$-alkyl, CN, C$_1$–C$_4$-alkyl which can be straight-chain or branched, saturated or unsaturated and optionally mono- or polysubstituted by halogen, C$_1$–C$_4$-alkoxy, methylenedioxy, ethylenedioxy, NH$_2$, C$_1$–C$_4$-alkylamino, NH-SO$_2$CH$_3$, COCH$_3$, COOH, COOC$_1$–C$_4$-alkyl, NO$_2$, CN or N$_3$, A is either a single bond, C$_1$–C$_4$-alkylene or C$_2$–C$_6$-alkenylene, and B is phenyl, naphthyl, pyridyl, pyrimidyl, furyl, thienyl, imidazolyl, C$_1$–C$_{20}$-alkyl which can be straight-chain or branched, and saturated or unsaturated by one or more double or triple bonds, where one or more methylene groups can be replaced by a keto group, by O, by NH or by N-alkyl(C$_1$–C$_4$), C$_3$–C$_7$-cycloalkyl which can be saturated or unsaturated, where a methylene group can optionally be replaced by a keto group and one or two methylene groups can optionally be replaced by O or NH, where the radical B can be mono- or polysubstituted by halogen, C$_1$–C$_4$-alkoxy, methylenedioxy, ethylenedioxy, NH$_2$C$_1$–C$_4$-alkylamino, NO—SO$_2$CH$_3$, CO—CH$_3$, COOH, COOC$_1$–C$_4$-alkyl, NO$_2$,CN or N$_3$, or A is a single bond and $R_1$ and B together are a C$_3$–C$_8$-alkylene or -alkenylene group, in which 2 methylene groups can additionally be bridged by means of a further C$_1$–C$_4$-alkylene chain, where one or more methylene groups can be replaced by a keto group, or by O, NH or N-alkyl(C$_1$–C$_4$) and where the ring formed from $R_1$ and B can optionally be mono- or polysubstituted by halogen, C$_1$–C$_4$-alkyl which can be straight-chain or branched, by C$_1$–C$_4$-alkoxy, methylenedioxy, ethylenedioxy, NH$_2$, C$_1$–C$_4$-alkylamino, NH-SO$_2$CH$_3$, CO—CH$_3$, COOH, COOC$_1$–C$_4$-alkyl, NO$_2$, CN or N$_3$, which comprises reacting an asymmetric alcohol of the formula I with a vinyl or isopropenyl diester of a C$_2$–C$_{10}$ alkane or a C$_2$–C$_{10}$ alkene dicarboxylic acid in the presence of a lipase as catalyst, and isolating the unreacted, enantiomerically-enriched alcohol of the formula I, and, optionally, isolating and hydrolyzing the ester formed by the process.

2. The process according to claim 1, wherein $R_1$ is COOH, CN, C$_1$–C$_4$-alkyl which is straight-chain or branched, saturated or unsaturated and is optionally mono- or polysubstituted by halogen, C$_1$–C$_4$-alkylamino, COOH, CN or N$_3$.

3. The process according to claim 1, wherein

A is a Single bond.

4. The process according to claim 1, wherein

B is phenyl, fury, imidazolyl, C$_1$–C$_{20}$-alkyl which can be straight-chain or branched, saturated or unsaturated by one or more double or triple bonds, where one or more methylene groups can be replaced by a keto group or by O, C$_3$–C$_7$-cycloalkyl which can be saturated or unsaturated, where a methylene group can optionally be replaced by a keto group and one or two methylene groups can optionally be replaced by O, where the radical B can be mono- or polysubstituted by halogen, C$_1$–C$_4$-alkoxy, C$_1$–C$_4$-alkylamino, CN or N$_3$ .

5. The process according to claim 1, wherein

A is a single bond and $R_1$ and B together are a C$_3$–C$_8$-alkylene group in which 2 methylene groups can additionally be bridged by means of a further C$_1$–C$_4$-alkylene group, where one or more methylene groups can be replaced by a keto group or O and where the ring formed from $R_1$ and B can optionally be mono- or polysubstituted by halogen, C$_1$–C$_4$-alkyl which can be straight-chain or branched, by C$_1$–C$_4$-alkoxy, C$_1$–C$_4$-alkylamino, CN or N$_3$.

* * * * *